United States Patent
Bailey et al.

(10) Patent No.: US 10,262,788 B2
(45) Date of Patent: Apr. 16, 2019

(54) METHOD TO ENABLE STANDARD ALTERNATING CURRENT (AC)/DIRECT CURRENT (DC) POWER ADAPTERS TO OPERATE IN HIGH MAGNETIC FIELDS

(71) Applicant: KONINKLIJKE PHILIPS N.V., Eindhoven (NL)

(72) Inventors: Paul Wayne Bailey, North Reading, MA (US); Donald Alan Forrer, Jr., Orlando, FL (US); Dimitri George Kostakis, Orlando, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 215 days.

(21) Appl. No.: 15/103,331

(22) PCT Filed: Dec. 11, 2014

(86) PCT No.: PCT/IB2014/066796
§ 371 (c)(1),
(2) Date: Jun. 10, 2016

(87) PCT Pub. No.: WO2015/087271
PCT Pub. Date: Jun. 18, 2015

(65) Prior Publication Data
US 2016/0322155 A1 Nov. 3, 2016

Related U.S. Application Data

(60) Provisional application No. 61/915,067, filed on Dec. 12, 2013.

(51) Int. Cl.
G01R 33/56 (2006.01)
H01F 27/36 (2006.01)
(Continued)

(52) U.S. Cl.
CPC ......... H01F 27/365 (2013.01); A61B 5/0555 (2013.01); G01R 33/28 (2013.01);
(Continued)

(58) Field of Classification Search
CPC .............. A61B 2562/182; A61B 18/18; A61B 2018/00791; A61B 5/0046; A61B 18/082;
(Continued)

(56) References Cited

U.S. PATENT DOCUMENTS 3,244,960 A 4/1966 Stevens
4,163,208 A * 7/1979 Merz ..................... B60C 23/007
200/61.25
(Continued)

FOREIGN PATENT DOCUMENTS

CN 101794659 8/2010
JP 60-033426 2/1985
(Continued)

*Primary Examiner* — Vinh P Nguyen (57) ABSTRACT

A power supply (10) and corresponding method (200) supply power in high external magnetic fields. A power converter system (12) converts input power to output power using one or more electromagnetic components (18). One or more ferrous bands (16) encircle the electromagnetic components (18) and shield the electromagnetic components (18) from the high external magnetic fields.

18 Claims, 6 Drawing Sheets

(51) Int. Cl.
*G01R 33/28* (2006.01)
*G01R 33/421* (2006.01)
*A61B 5/055* (2006.01)
*G01R 33/38* (2006.01)
*G01R 33/385* (2006.01)
*G01R 33/54* (2006.01)
*H02M 7/00* (2006.01)
*H05K 7/20* (2006.01)

(52) U.S. Cl.
CPC ....... *G01R 33/3804* (2013.01); *G01R 33/385* (2013.01); *G01R 33/421* (2013.01); *G01R 33/546* (2013.01); *G01R 33/56* (2013.01); *H02M 7/003* (2013.01); *H05K 7/2089* (2013.01)

(58) Field of Classification Search
CPC .... A61B 5/01; G01R 33/3804; G01R 33/422; G01R 33/3806; G01R 33/385; G01R 33/48; G01R 33/381; G01R 33/3875; G01R 33/5608; G01R 33/34007; G01R 33/3614; G01R 33/3802; G01R 33/3854; G01R 33/445; G01R 33/543; G01R 33/546; G01R 33/56; G01R 33/36; G01R 33/38; G01R 33/383; G01R 33/3852; G01R 33/3856; G01R 33/3858; G01R 33/28; G01R 33/283; G01R 33/421; G01R 33/4806; H01F 7/02; H01F 7/06; H01F 6/06; H01F 27/36; H01F 27/365; H01F 38/14; H01F 7/202; H01F 27/2823; H01F 37/00; H01F 7/0247; H01F 7/0252; H01F 2003/005; H01F 27/2804; H01F 5/003; H01F 27/42; A61F 7/00; A61F 7/007; A61F 2007/0056; A61F 2007/0093; A61F 2007/0095; A61F 2007/0096; A61F 2210/009; H04B 5/0037; H04B 5/0093; H04B 5/0081; H04B 5/0075; H04B 5/0087; H05K 7/02; H05K 7/2089
See application file for complete search history.

(56) References Cited

U.S. PATENT DOCUMENTS

| | | | | |
|---|---|---|---|---|
| 4,700,131 | A | * 10/1987 | Miller | .............. G01R 19/02 |
| | | | | 310/68 C |
| 5,091,823 | A | 2/1992 | Kanbara | |
| 6,317,618 | B1 | 11/2001 | Livni | |
| 6,950,291 | B1 * | 9/2005 | Andres | .............. H01F 27/362 |
| | | | | 361/118 |
| 8,797,032 | B2 * | 8/2014 | Ookawa | .............. A61B 5/055 |
| | | | | 324/314 |
| 9,585,574 | B2 | 3/2017 | Nelson | |
| 2002/0077560 | A1 | 6/2002 | Kramer | |
| 2002/0169415 | A1 | 11/2002 | Staats | |
| 2005/0192473 | A1 | 9/2005 | Loenneker-Lammers | |
| 2011/0210739 | A1 | 9/2011 | Ham | |
| 2013/0265811 | A1 * | 10/2013 | Shiomi | .............. H02M 7/003 |
| | | | | 363/146 |

FOREIGN PATENT DOCUMENTS

| | | |
|---|---|---|
| JP | 63239908 | 10/1988 |
| JP | 02-000799 | 1/1990 |
| JP | 2010161890 | 7/2010 |
| WO | 2006/081434 | 8/2006 |
| WO | 2013/061200 | 5/2013 |

* cited by examiner

METHOD TO ENABLE STANDARD ALTERNATING CURRENT (AC)/DIRECT CURRENT (DC) POWER ADAPTERS TO OPERATE IN HIGH MAGNETIC FIELDS

CROSS REFERENCE TO RELATED APPLICATIONS

This applications is the U.S. National Phase application under 35 U.S.C. § of International Application No. PCT/IB2014/066796, filed Dec. 11, 2014, published as WO 2015/087271 on Jun. 18, 2015, which claims the benefit of U.S. Provisional Patent Application Number 61/915,067 filed Dec. 12, 2013. These applications are hereby incorporated by reference herein.

The present application relates generally to power supplies. It finds particular application in conjunction alternating current (AC)/direct current (DC) power adapters for medical devices used in high external magnetic fields, and will be described with particular reference thereto. However, it is to be understood that it also finds application in other usage scenarios, and is not necessarily limited to the aforementioned application.

Traditional methods of converting AC line power to isolated DC power involve the use of electromagnetic transformers and inductors. When an AC/DC power adapter employing such methods is used in high external magnetic fields, such as in the magnet room of a magnetic resonance imaging (MRI) facility, the power adapter must usually be positioned and mechanically secured at a safe distance from the magnet. Without securing the power adapter at a safe distance, the electromagnetic transformer and inductors can saturate from the high external magnetic field. This can cause the power adapter to lose its ability to convert power, overheat, or be damaged. Further, electromagnetic transformers have a significant magnetic attraction and without securing the power adapter at a safe distance, the power adapter can create a safety hazard by becoming a projectile.

A challenge with securing the power adapter away from the magnet is that often times a device powered by the power adapter needs to be used in close proximity to the magnet. Typically, this challenge is addressed by providing power via a long cable extending from the power adapter to the device, or by providing power from batteries local to the device and merely using the power adapter to charge the batteries. However, employing a long cable reduces portability and can pose a safety risk to both the device and users of the device since the users can trip over the cable. Further, batteries are limited in the amount of power that can be provided and have a useful life much shorter than the device itself.

The present application provides a new and improved system and method which overcome these problems and others.

In accordance with one aspect, a power supply for supplying power in high external magnetic fields is provided. The power supply includes a power converter system which converts input power to output power using one or more electromagnetic components. The power supply further includes one or more ferrous bands which encircle the electromagnetic components and shield the electromagnetic components from the high external magnetic fields.

In accordance with another aspect, a method for supplying power in high external magnetic fields is provided. The method includes providing a power converter system which converts input power to output power using one or more electromagnetic components. The method further includes shielding the electromagnetic components from the high external magnetic fields with one or more ferrous bands which encircle the electromagnetic components.

In accordance with another aspect, a medical device for use in high external magnetic fields is provided. The device includes a high priority load and a low priority load. The device further includes a power supply which powers the high and low priority loads. The power supply includes one or more ferrous bands which encircle electromagnetic components of the power supply and shield the electromagnetic components from the high external magnetic fields. The power supply further includes a thermal control system which disables power to the low priority load in response to one or more temperatures of the power supply exceeding thresholds.

One advantage resides in minimizing magnetic immunity issues.

Another advantage resides in an alternating current (AC)/direct current (DC) power adapter integral with the device being powered.

Another advantage resides in closer positioning to a magnet producing high external magnetic fields.

Another advantage resides in improved portability.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The present application minimizes the effects of high external magnetic field on a typical alternating current (AC)/direct current (DC) power adapter by adding mechanical, and optionally electrical features, to the power adapter that lower the magnetic and thermal stresses on the electromagnetic components of the power adapter. The mechanical features include ferrous bands around sensitive electromagnetic components. The electrical features include temperature sensors on electromagnetic components of the power adapter and a controller controlling power to the loads of the power adapter based on measurements of the temperature sensors. When temperature measurements exceed predetermined limits (e.g., experimentally determined), non-essential loads are disabled. Advantageously, by applying the mechanical, and optionally the electrical features, to a typical AC/DC power adapter, the AC/DC power adapter can operate reliably in close proximity to a main magnet of a magnetic resonance imaging (MRI) system.

Figure 1:
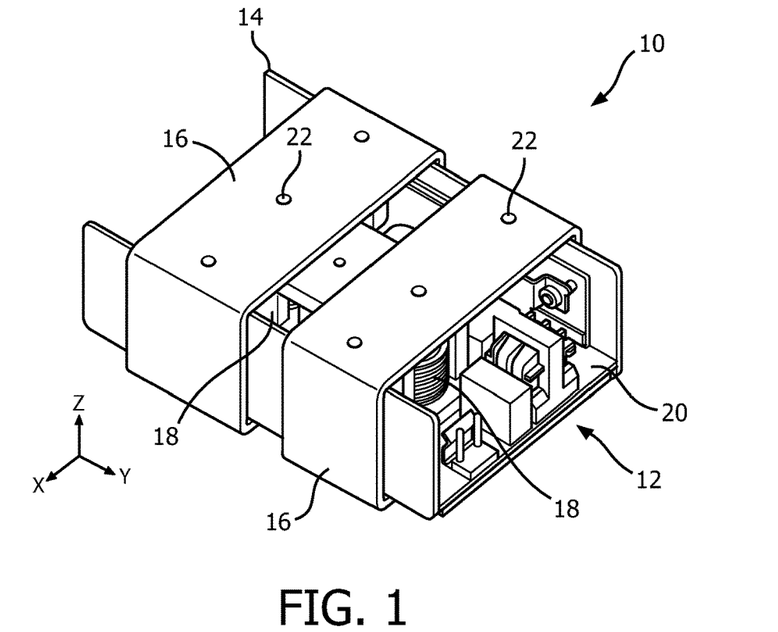
FIG. 1 illustrates an alternating current (AC)/direct current (DC) power adapter for use in high external magnetic fields.
Figure 2A:
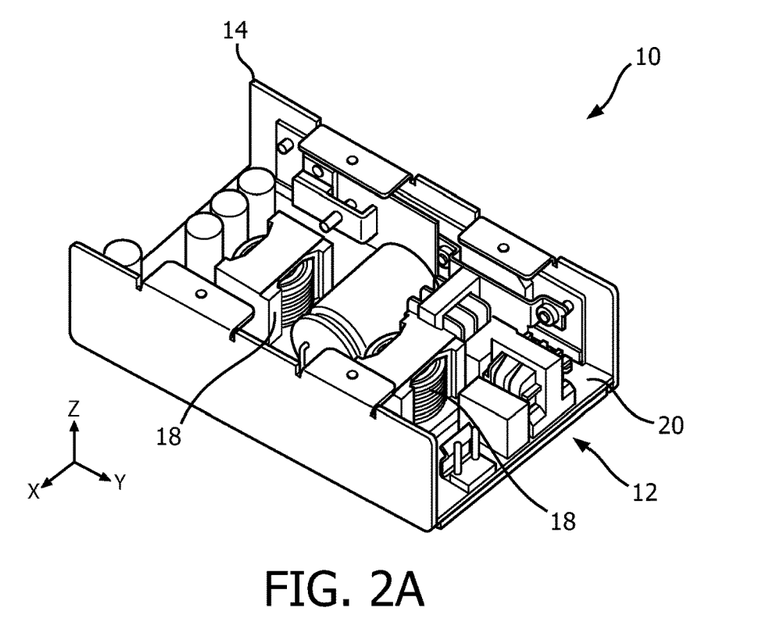
FIG. 2A illustrates an AC/DC power converter system and a housing, of FIG. 1.
Figure 2B:
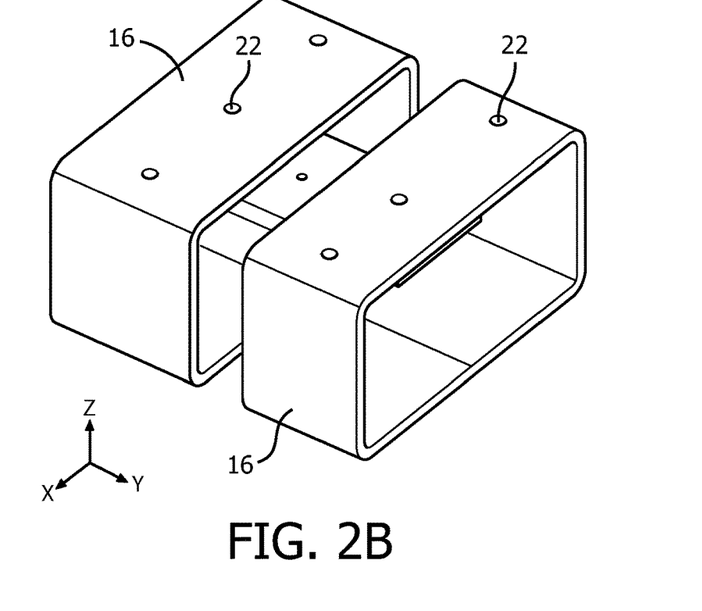
FIG. 2B illustrates ferrous bands of FIG. 1.

With reference to FIG. 1, an AC/DC power adapter 10 for use in high external magnetic fields is provided. As used herein, a high external magnetic field is a magnetic field above 2000 gauss (G). The power adapter 10 includes an AC/DC power converter system 12, a housing 14 for the AC/DC power converter system 12, and ferrous bands 16. FIG. 2A illustrates the AC/DC power converter system 12 and the housing 14 without the ferrous bands 16, and FIG. 2B illustrates the ferrous bands 16 without the AC/DC power converter system 12 and the housing 14.

The AC/DC power converter system 12 receives AC power from an external source, such as a power grid or generator, and converts the received AC power to DC power. The DC power is then output for use by an external load. While the specific design of the AC/DC power converter system 12 is irrelevant to the present application, the AC/DC power converter system 12 uses electromagnetic components 18 (best seen in FIG. 2A) that are sensitive to high external magnetic fields, such as transformers and/or inductors. Absent shielding from high external magnetic fields, the sensitive electromagnetic components 18 can saturate from the high external magnetic field, thereby causing improper operation, overheating or damage. The AC/DC power converter system 12 is typically integrated with a circuit board 20 mounted to the housing 14.

To mitigate the effects of high external magnetic fields on the sensitive electromagnetic components 18, the ferrous bands 16 encircle the sensitive electromagnetic components 18. The ferrous bands 16 are typically completely solid with a uniform thickness (illustrated in the Z direction), width (illustrated in the Y direction) and length (illustrated in the X direction). However, the ferrous bands 16 can also have holes 22, for example, running through the thickness of the ferrous bands 16. The holes 22 can be used for mounting, as well as for reducing the mass of the ferrous bands 16 and/or for reducing magnetic pull force. Further, as discussed below, the width of each ferrous band 16 is typically limited to the width of the sensitive electromagnetic components 18 to limit the amount of ferrous material and the magnetic pull. Hence, there is typically no one ferrous band 16 spanning the entire width of the power adapter 10. Rather, there are typically multiple spaced ferrous bands 16 spanning the width of the power adapter 10.

Typically, there is a one-to-one correspondence between the ferrous bands 16 and the sensitive electromagnetic components 18. However, a one-to-many correspondence and a mix of the two correspondences are also contemplated. A one-to-many correspondence is employed for sensitive electromagnetic components 18 that do not overlap in the two dimensional (2D) projection space defined by the axes of the thickness and the width of the ferrous bands 16. A one-to-many correspondence is employed for sensitive electromagnetic components 18 overlapping in the two-dimensional (2D) projection space, each overlapping set of sensitive electromagnetic components 18 encircled by a ferrous band 16. Hence, each of the ferrous bands 16 encircles a set of one or more sensitive, overlapping electromagnetic components 18. Selecting the proper correspondence advantageously reduces the amount of ferrous material used by the ferrous bands 16 and therefore magnetic pull. A ferrous band 16 for a set 18 is oriented relative to the set 18 so the magnetic flux induced to flow in the ferrous band 16 by a high external magnetic field flows perpendicular to the magnetic fields produced by the set 18.

When designing a ferrous band 16 for a set of one or more sensitive, overlapping electromagnetic components 18, the width of the ferrous band 16 is greater than or equal to the width of the set 18. Even more, the length of the ferrous band 16 is sufficient to encircle the set 18 with the band positioned a sufficient distance (e.g., ¼ inch) from the set 18 to prevent the ferrous band 16 from becoming part of the set 18 and interfering with operation of the set 18. Subject to the foregoing qualifications, one or more of the material (e.g., 1018 steel coated for corrosion), the width, the length and the thickness (e.g., 10 gauge) of the ferrous band 16 are optimized so as to minimize the mass of the ferrous band 16, while at the same time providing the ferrous band 16 with a sufficient mass to shield the set 18 from magnetic fields of a predetermined strength (e.g., 3 Tesla (T)). The amount of ferrous material is minimized to limit magnetic pull. Typically, the thickness and the material of the ferrous band 16 are optimized, while the width and the length of the ferrous band 16 are set at the minimum values needed to achieve the foregoing qualifications.

The variables are optimized typically by minimizing or maximizing a model of the ferrous band 16 that scores the ferrous band 16 based on the mass and the ability to shield the set 18. For example, where higher scores indicate that the ferrous band 16 better achieves the design considerations noted above, the model is maximized. Both the mass and the ability to shield are defined in terms of the variables to be optimized, such as the width, the length, the thickness, and the material of the ferrous band 16. Other variables can further be included.

As described above, each of the ferrous bands 16 encircles a set of one or more sensitive electromagnetic components 18. Hence, the correspondence between the ferrous bands 16 and the sensitive electromagnetic components 18 was described as a one-to-one correspondence, a one-to-many correspondence, or a mix of these correspondences. In some instances, a ferrous band 16 can be replaced by multiple ferrous bands 16 spaced (e.g., evenly spaced) along the width of the ferrous band 16 being replaced, so long as the spacing is not so large as to compromise the shielding provided to the set 18. Hence, in some instances, the correspondence between the ferrous bands 16 and the sensitive electromagnetic components 18 can be a one-to-one correspondence, a one-to-many correspondence, a many-to-one correspondence, a many-to-man correspondence, or a mix of these correspondences The ferrous bands 16 are suitably mounted directly to the housing 14, which can advantageously be employed to ensure that there is adequate spacing between the ferrous bands 16 and the sensitive electromagnetic components 18. For example, as illustrated, the ferrous bands 16 are directly mounted to the housing 14 and positioned around the housing 14, which has a width (Y direction) and a length (X direction) to ensure proper spacing between the ferrous bands 16 and the sensitive electromagnetic components 18. Notwithstanding that the ferrous bands 16 are suitably mounted directly to the housing 14, other approaches for mounting the ferrous bands 16 around the sensitive electromagnetic components 18 are contemplated. For example, the ferrous bands 16 can be mounted indirectly to the housing 14 by way of the circuit board 20 or some other component of the power adapter 10.

By encircling the sensitive electromagnetic components 18 as described above, the ferrous bands 16 reduce the exposure of the sensitive electromagnetic components 18 to magnetic fields. This reduces the magnetic and thermal stresses placed on the sensitive electromagnetic components

Figure 3:
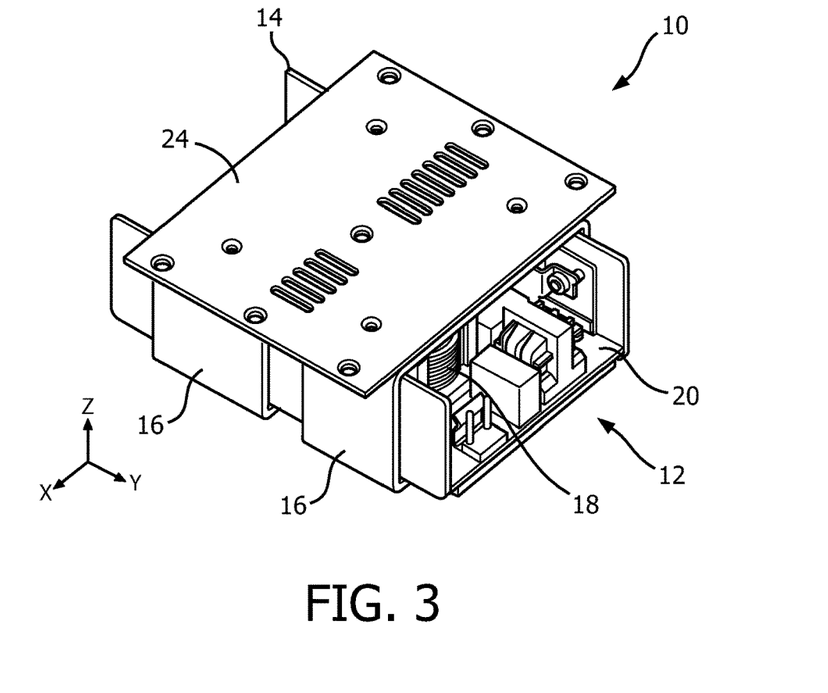
FIG. 3 illustrates the power adapter of FIG. 1 with a heat sink mounted thereto.

18. The ferrous bands 16 further reduce thermal stresses placed upon the sensitive electromagnetic components 18, and more generally the power adapter 10, by providing the power adapter 10 with additional surface area for removing heat from the power adapter 10 (e.g., convectively, radiatively and conductively). As illustrated in FIG. 3, heat removal can be enhanced with a heat sink 24 mounted to the power adapter 10. For example, as illustrated, the heat sink 24 can be a plate mounted to, for example, the housing 14 or the ferrous bands 16. The heat sink 24 is suitably formed from a material with a high thermal conductivity, such as aluminum or copper.

Figure 4:
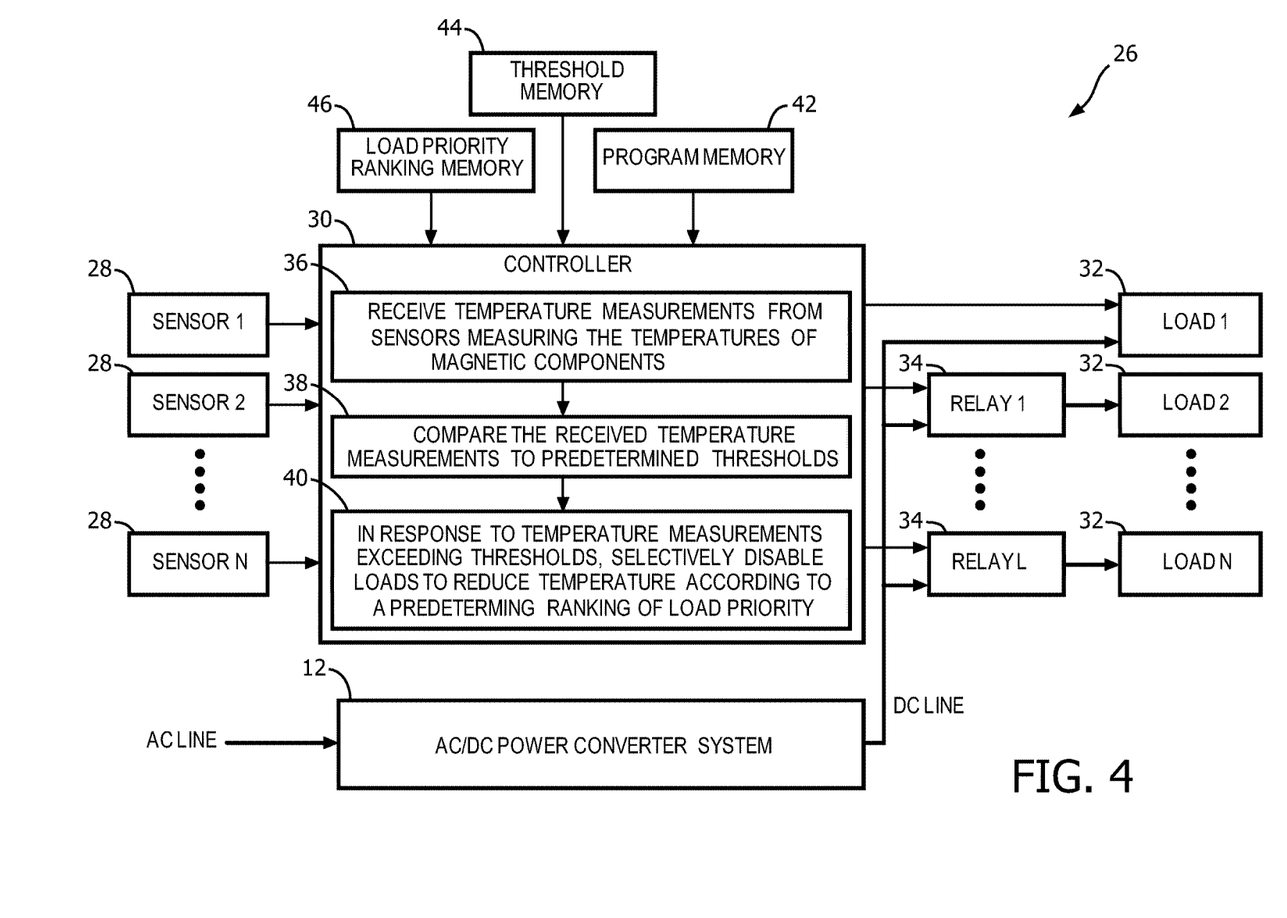
FIG. 4 illustrates a thermal control system of the power adapter of FIG. 1.

With reference to FIG. 4, the power adapter 10 can further include a thermal control system 26 managing current drawn from the power adapter 10 to limit the thermal stress placed on the power adapter 10. The thermal control system 26 is housed by the housing 14 and typically integrated with a circuit board 20 mounted to the housing 14. In some instances, the thermal control system 26 shares a circuit board 20 with the AC/DC power converter system 12. The thermal control system 26 includes one or more temperature sensors 28 (illustrated as M>=1 sensors) measuring the temperatures of components of the AC/DC power converter system 12, such as the sensitive electromagnetic components 18, that may overheat due to magnetic saturation effects. Further, the thermal control system 26 includes a controller 30 managing the provisioning of DC power from the AC/DC power converter system 12 to one or more loads 32 (illustrated as N>=1 loads).

The provisioning of DC power to loads 32 can be managed through control of one or more switches or relays 34 of the thermal control system 26. Typically, there is a one-to-one correspondence between loads 32 and the switches or relays 34, but other correspondences are contemplated. As illustrated, all the loads 32 except LOAD 1 are managed by L>=1 switches or relays. The provisioning of DC power to loads 32 can additionally or alternatively be managed through control of the loads 32 themselves by enabling or disabling the loads 32. For example, the chip-enable pin of an integrated circuit that controls a load 32 can be employed to enable or disable the load 32. As illustrated, LOAD 1 is managed by enabling or disabling the load.

The controller 30 continuously receives 36 temperature measurements from the sensors 28, for example, at predetermine intervals. Upon receiving temperature measurements, the controller 30 compares 38 the temperature measurements to corresponding thresholds indicating the point where temperature is deemed too high. The thresholds are predetermined by an operator or manufacture of the thermal control system 26 and can be determined, for example, based on normal operating temperatures of the power adapter 10. Typically, the thresholds are specific to a sensor 28, but a common threshold is also contemplated. In response to an individual sensor 28 or a predetermined combination of sensors 28 reporting excessive temperatures, the controller 30 selectively disables 40 the loads 32 of the AC/DC power converter system 12 according to a load priority ranking. The loads 32 are gradually disabled from lowest priority to highest priority according to the load priority ranking until the one or more sensors 28 reporting excessive temperatures indicate decreasing temperatures. For example, where the power adapter 10 provides power to a main load and a secondary load, the secondary load can be disabled first. After temperatures return to normal, the disabled loads can be gradually enabled from highest priority to lowest priority.

The controller 30 can be an analog circuit, a digital circuit, or a combination of analog and digital circuitry. Further, the controller 30 can be specifically designed for thermal control or a general purpose controller executing a program on a program memory 42, as illustrated. Where the controller 30 is a general purpose controller, the thresholds and the load priority ranking are each stored on a corresponding memory 44, 46. As illustrated, individual memories 42, 44, 46 for the thresholds, the load priority, and the program can be employed. Alternatively, these memories 42, 44, 46 can be combined in different combinations. For example, the thresholds, the load priority ranking and the program can all share the same memory.

Figure 5:
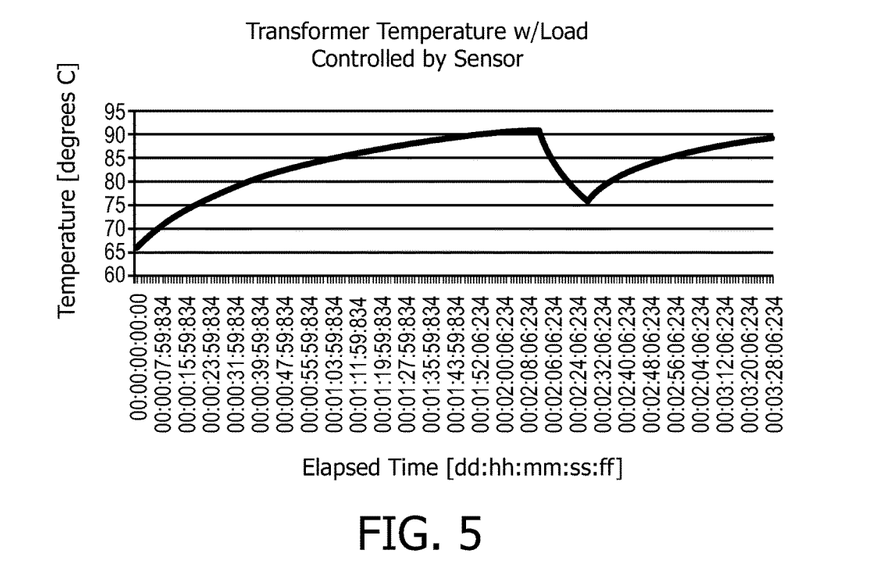
FIG. 5 illustrates a graph of temperature over time for the power adapter of FIG. 1 when using the thermal control system of FIG. 4.

With reference to FIG. 5, a graph illustrates temperature over time for an embodiment of the power adapter 10 employing the thermal control system 26. Temperature is identified in degrees Celsius (C), and time is identified in terms of days (dd), hours (hh), minutes (mm), seconds (ss), and milliseconds (fff). As can be seen, the temperature rises until about 90 degrees C. This rise is caused by the power adapter 10 being moved closer to a source of a high external magnetic field. Once 90 degrees C. is reached, a non-essential load, such as a battery charger, is disabled, thereby reducing the temperature of the power adapter 10. However, after the temperature drops, the temperature once again rises. This rise is caused by the non-essential load being reapplied once a safe operating temperature has been reached.

Figure 6:
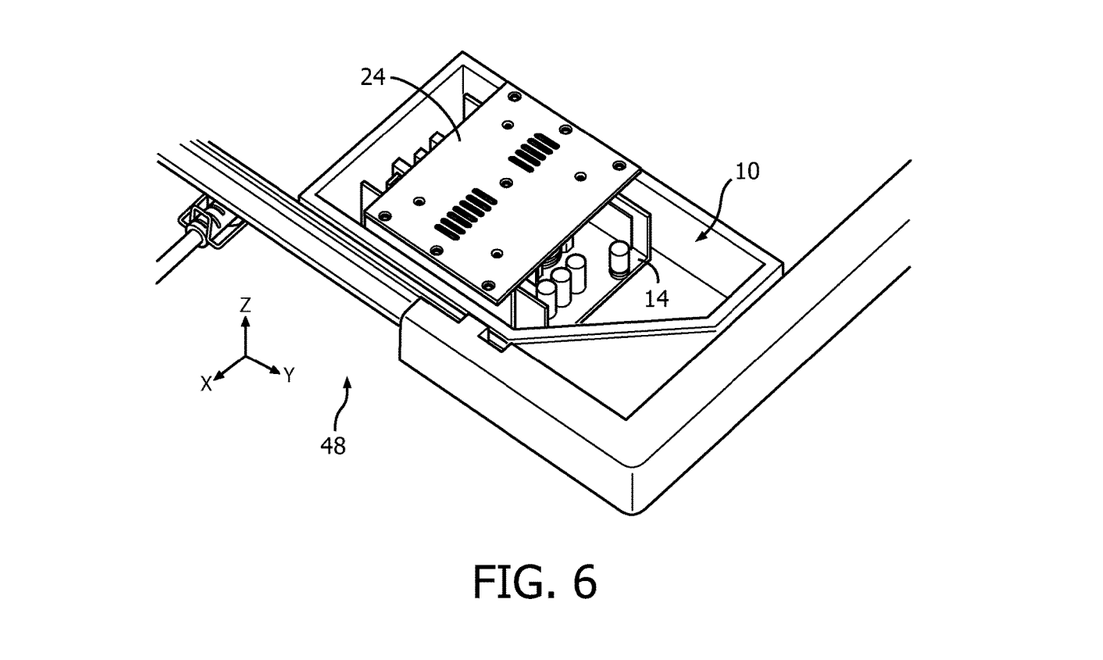
FIG. 6 illustrates a portion of a device including the power adapter and the heat sink of FIGS. 1 and 3, respectively.

With reference to FIG. 6, a device 48 including the power adapter 10 and the heat sink 24 is illustrated. Typically, the power adapter 10 is integrated within a portion of the device 48 attached to a heavy mass. The heavy mass provides heat sinking for the device 48 and the power adapter 10, while also countering the force of magnetic pull. This portion of the device 48 is typically kept close to the floor. Further, the power adapter 10 can be enclosed in a Faraday cage in order minimize the radiated emissions that might interfere with the device 10 or systems external to the device, such as an MRI system. In some instances, the device 10 is a medical device operated proximate to the main magnet of an MRI system. Such devices include patient monitors, displays, entertainment devices, infusion pumps, injectors, motors, anesthesia workstations, cameras, battery chargers, and communication devices.

Figure 7:
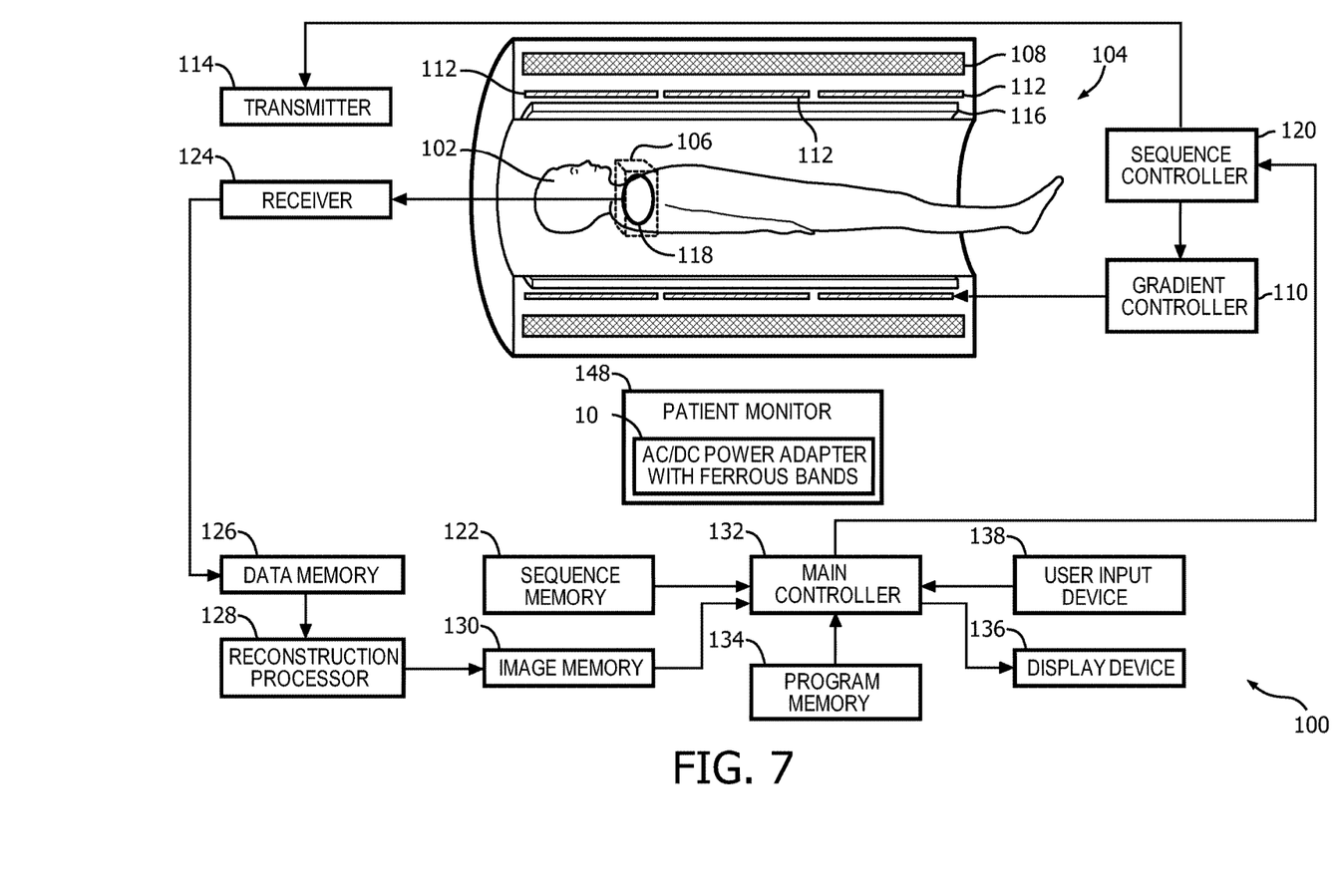
FIG. 7 illustrates a magnetic resonance imaging (MRI) system with the power adapter of FIG. 1 positioned proximate a main magnet.

With reference to FIG. 7, an MRI system 100 within which the device 48 can be employed is provided. The device 48 is illustrated as a patient monitor. The MRI system 100 uses magnetic resonance (MR) to generate one or more diagnostic images of a target volume of a patient 102. The system 100 includes a scanner 104 defining an imaging (or scan) volume 106 sized to accommodate the target volume. A patient support can be employed to support the patient 102 and to position the target volume near the isocenter of the imaging volume 106.

The scanner 104 includes a main magnet 108 that creates a strong, static $B_0$ magnetic field extending through the imaging volume 106. The main magnet 108 typically employs superconducting coils to create the static $B_0$ magnetic field. However, the main magnet 108 can also employ permanent or resistive magnets. Insofar as superconducting coils are employed, the main magnet 108 includes a cooling system, such as a liquid helium cooled cryostat, for the superconducting coils. The strength of the static $B_0$ magnetic field is commonly one of 0.23 Tesla, 0.5 Tesla, 1.5 Tesla, 3 Tesla, 7 Tesla, and so on in the imaging volume 106, but other strengths are contemplated.

A gradient controller 110 of the scanner 104 is controlled to superimpose magnetic field gradients, such as x, y and z gradients, on the static $B_0$ magnetic field in the imaging volume 106 using a plurality of magnetic field gradient coils 112 of the scanner 104. The magnetic field gradients spatially encode magnetic spins within the imaging volume 106. Typically, the plurality of magnetic field gradient coils 112 include three separate magnetic field gradient coils spatially encoding in three orthogonal spatial directions.

Further, one or more transmitters 114, such as a transceiver, are controlled to transmit $B_1$ resonance excitation and manipulation radiofrequency (RF) pulses into the imaging volume 106 with one or more transmit coil arrays, such as a whole body coil 116 and/or a surface coil 118, of the scanner 104. The $B_1$ pulses are typically of short duration and, when taken together with the magnetic field gradients, achieve a selected manipulation of magnetic resonance. For example, the $B_1$ pulses excite the hydrogen dipoles to resonance and the magnetic field gradients encode spatial information in the frequency and phase of the resonance signal. By adjusting the RF frequencies, resonance can be excited in other dipoles, such as phosphorous, which tend to concentrate in known tissues, such as bones.

A sequence controller 120 controls the gradient controller 110 and/or the transmitters 114 according to imaging sequences to produce spatially encoded MR signals within the imaging volume 106. An imaging sequence defines a sequence of $B_1$ pulses and/or magnetic field gradients. Further, the imaging sequences can be received from a device or system being remote or local to the sequence controller, such as a sequence memory 122.

One or more receivers 124, such as a transceiver, receive the spatially encoded magnetic resonance signals from the imaging volume 106 and demodulate the received spatially encoded magnetic resonance signals to MR data sets. The MR data sets include, for example, k-space data trajectories. To receive the spatially encoded magnetic resonance signals, the receivers 124 use one or more receive coil arrays, such as the whole body coil 116 and/or the surface coil 118, of the scanner 104. The receivers 124 typically store the MR data sets in a data memory 126.

A reconstruction processor 128 reconstructs the MR data sets into MR images or maps of the imaging volume 106. This includes, for each MR signal captured by the MR data sets, spatially decoding the spatial encoding by the magnetic field gradients to ascertain a property of the MR signal from each spatial region, such as a pixel or voxel. The intensity or magnitude of the MR signal is commonly ascertained, but other properties related to phase, relaxation time, magnetization transfer, and the like can also be ascertained. The MR images or maps are typically stored in an image memory 130.

A main controller 132 controls the reconstruction processor 128 and the sequence controller 120 to generate one or more diagnostic images of the target volume using one or more scans of the target volume. For each scan, the target vessel is positioned within the imaging volume 106. For example, the patient 102 is positioned on the patient support. The surface coil 118 is then positioned on the patient 102 and the patient support moves the target volume into the imaging volume 106. The size of the imaging volume 106 can vary between scans.

Once the target volume is positioned within the imaging volume 106, the main controller 132 controls the sequence controller 120 according to scan parameters, such as number of slices, and provides the sequence controller 120 with an imaging sequence. The imaging sequence can, for example, be stored in the sequence memory 122. As noted above, an imaging sequence defines a sequence of $B_1$ pulses and/or magnetic field gradients that produce spatially encoded MR signals from the imaging volume 106. Further, the main controller 132 can control the receivers 124 according to scan parameters. For example, the main controller 132 can adjust the gain of the receivers 124.

The main controller 132 can carry out the foregoing functionality by software, hardware or both. Where the main controller 132 employs software, the main controller 132 includes at least one processor executing the software. The software is suitably stored on a program memory 134, which can be local or remote from the main controller 42. Further, the main controller 132 can be managed by a user using a graphical user interface presented to the user by way of a display device 136 and a user input device 138. The user can, for example, initiate imaging, display images, manipulate images, etc.

Notwithstanding that the reconstruction processor 128 and the sequence controller 120 were illustrated as external to the main controller 132, it is to be appreciated that one or both of these components can be integrated with the main controller 132 as software, hardware or a combination of both. For example, the reconstruction processor 128 can be integrated with the main controller 132 as a software module executing on the at least one processor of the main controller 132.

While the foregoing discussion focused on an AC/DC power adapter, those skilled in the art will appreciate that the ferrous bands 16 and the thermal management system 26 are equally amenable to other types of power supplies. The AC/DC power converter system 12 is merely replaced with the appropriate type of power converter system, such as a DC/DC power converter system. The ferrous bands 16 are applied to the sensitive electromagnetic components 18 in the same manner described above. Further, the thermal management system 26 is applied to electromagnetic components 18 and loads 30 in the same manner described above.

Figure 8:
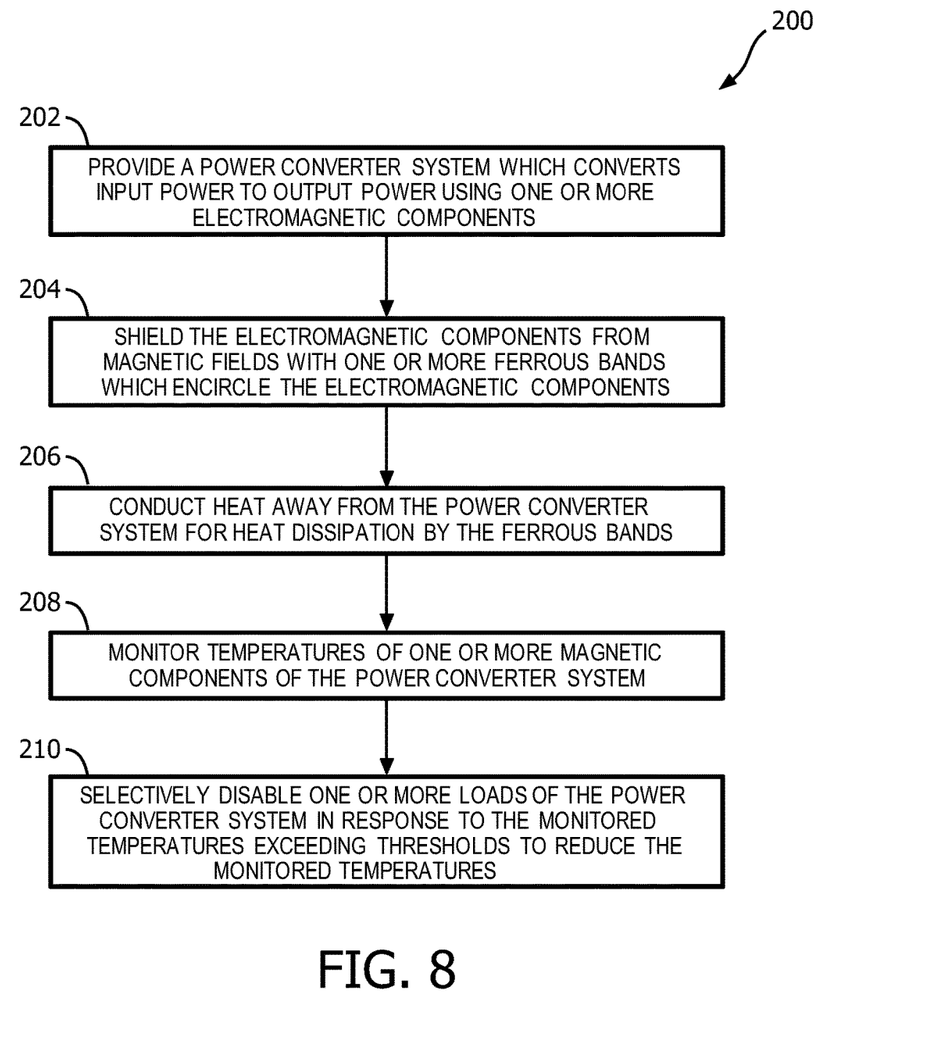
FIG. 8 illustrates a method for supplying power in high external magnetic fields using the power adapter of FIG. 1.

With reference to FIG. 8, a method 200 for supplying power in external magnetic fields according to the above discussion is provided. The method 200 is performed by a power supply, such as the AC/DC power adapter 10, in a high external magnetic field. A high external magnetic field is typically a magnetic field greater than 2000 G. Such magnetic fields are common proximate (e.g., within a few feet) of a main magnetic 108 of a magnetic resonance imaging MRI system 100.

The method 200 includes providing 202 a power converter system 12 which converts input power to output power using one or more electromagnetic components 18. The power converter system 12 is typically an AC/DC power converter system, but other types of power converter systems are contemplated. The electromagnetic components 18 are shielded 204 from the high external magnetic fields with one or more ferrous bands 16 which encircle the electromagnetic components 18. The ferrous bands 16 are designed to minimize the mass of the ferrous bands 16, while at the same time providing sufficient mass to shield the electromagnetic components 18 from the high external magnetic fields. The ferrous bands 16, in addition to providing shielding, conduct 206 heat away from the power converter system 12 for heat dissipation.

To enhance thermal management, the method 200 further includes monitoring 208 temperatures of one or more magnetic components 18 of the power converter system 12 and selectively disabling 210 one or more loads 32 of the power converter system 12 in response to the monitored temperatures exceeding thresholds to reduce the monitored temperatures. The selective disabling includes gradually disabling the loads 32 according to a load priority ranking from low to high until the excessive, monitored temperatures begin dropping. For example, a new load can be disabled every predetermined number of seconds, such as 10 seconds, until the excessive, monitored temperatures begin dropping.

As used herein, a memory includes any device or system storing data, such as a random access memory (RAM) or a read-only memory (ROM). Further, as used herein, a processor includes any device or system processing input device to produce output data, such as a microprocessor, a microcontroller, a graphic processing unit (GPU), an application-specific integrated circuit (ASIC), an FPGA, and the like; a controller includes any device or system controlling another device or system; a user input device includes any device, such as a mouse or keyboard, allowing a user of the user input device to provide input to another device or system; and a display device includes any device for displaying data, such as a liquid crystal display (LCD) or a light emitting diode (LED) display.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A power supply for supplying power in high external magnetic fields, the power supply comprising:
   a power converter system which converts input power to output power using two or more electromagnetic components; and
   one or more ferrous bands which encircle the electromagnetic components and shield the electromagnetic components from the high external magnetic fields;
   wherein the two or more electromagnetic components overlap in a two dimensional (2D) projection space defined by axes of the thickness and the width of the ferrous bands;
   and further including:
   a thermal control system which:
   monitors temperatures of one or more magnetic components of the power converter system; and
   selectively disables one or more loads of the power converter system in response to the monitored temperatures exceeding thresholds to reduce the monitored temperatures by gradually disabling the loads according to a load priority ranking from low to high until the excessive, monitored temperatures begin dropping.

2. The power supply according to claim 1, wherein the high magnetic field is greater than 2000 gauss (G).

3. The power supply according to claim 1, wherein the power converter system includes an alternating current (AC) to direct current (DC) converter.

4. The power supply according to claim 1, wherein the mass of the ferrous bands is minimal to reduce magnetic pull, while at the same time being sufficient to shield the electromagnetic components from the high external magnetic fields.

5. The power supply according to claim 1, wherein the set of ferrous bands includes a single ferrous band, the width of the ferrous band being at least as great as the width of the set of electromagnetic components, and the length of the ferrous band being sufficient to encircle the set of electromagnetic components with the ferrous band positioned a sufficient distance from the set of electromagnetic components to prevent the ferrous band from interfering with operation of the set of electromagnetic components.

6. The power supply according to claim 1, wherein the set of ferrous bands includes a plurality of ferrous bands spaced along the width of the set of ferrous bands, the width of the set of ferrous bands being at least as great as the width of the set of electromagnetic components, and the length of the set of ferrous bands being sufficient to encircle the set of electromagnetic components with the set of ferrous bands positioned a sufficient distance from the set of electromagnetic components to prevent the set of ferrous bands from interfering with operation of the set of electromagnetic components.

7. The power supply according to claim 1, wherein the ferrous bands are arranged to provide the power converter system with conduction paths for heat dissipation.

8. A device for use in a high external magnetic field, the device including:
   one or more loads; and
   the power supply according to claim 1, the power supply providing power to the loads.

9. A medical system comprising:
   a magnetic resonance imaging (MRI) scanner including a main magnetic which generates a high external magnetic field; and
   the power supply according to claim 1 positioned proximate to the main magnetic and providing power to a load.

10. A method for supplying power in high external magnetic fields, the method comprising:
    providing a power converter system which converts input power to output power using one or more electromagnetic components; and
    shielding the electromagnetic components from the high external magnetic fields with one or more ferrous bands which encircle the electromagnetic components;
    monitoring temperatures of one or more magnetic components of the power converter system; and
    selectively disabling one or more loads of the power converter system in response to the monitored temperatures exceeding thresholds to reduce the monitored temperatures by disabling the loads according to a load priority ranking from low to high until the excessive, monitored temperatures begin dropping.

11. The method according to claim 10, further including:
    minimizing the mass of the ferrous bands to reduce magnetic pull, while at the same time providing sufficient mass to shield the electromagnetic components from the high external magnetic fields.

12. The method according to claim 10, further including:
    conducting heat away from the power converter system for heat dissipation by the ferrous bands.

13. The method according to claim 10, further including:
    positioning the power converter system proximate a main magnetic of a magnetic resonance imaging (MRI) system, the main magnet generating the high external magnetic field.

14. A power supply for supplying power in high external magnetic fields, the power supply comprising:
    a power converter system which converts input power to output power using one or more electromagnetic components; and
    a thermal control system including:

one or more temperature sensors that monitor temperature of the one or more magnetic components of the power converter system; and a controller that selectively disables one or more loads of the power converter system in response to the monitored temperature exceeding thresholds to reduce the monitored temperatures by gradually disabling the loads according to a load priority ranking from low to high until the excessive, monitored temperatures begin dropping.

15. The power supply according to claim 14, further comprising one or more ferrous bands which encircle the electromagnetic components and shield the electromagnetic components from the high external magnetic fields.

16. The power supply according to claim 15, wherein the ferrous bands includes a single ferrous band, the width of the ferrous band being at least as great as the width of the set of electromagnetic components, and the length of the ferrous band being sufficient to encircle the set of electromagnetic components with the ferrous band positioned a sufficient distance from the set of electromagnetic components to prevent the ferrous band from interfering with operation of the set of electromagnetic components.

17. The power supply according to claim 15, wherein the ferrous bands includes a plurality of ferrous bands spaced along the width of the set of ferrous bands, the width of the set of ferrous bands being at least as great as the width of the set of electromagnetic components, and the length of the set of ferrous bands being sufficient to encircle the set of electromagnetic components with the set of ferrous bands positioned a sufficient distance from the set of electromagnetic components to prevent the set of ferrous bands from interfering with operation of the set of electromagnetic components.

18. The power supply according to claim 15, wherein the ferrous bands are arranged to provide the power converter system with conduction paths for heat dissipation.

* * * * *